(12) United States Patent
Boling et al.

(10) Patent No.: US 9,757,572 B2
(45) Date of Patent: Sep. 12, 2017

(54) IMPLANTABLE MEDICAL DEVICE AND METHOD FOR LASER PROCESSING

(71) Applicant: AUTONOMIC TECHNOLOGIES, INC., Redwood City, CA (US)

(72) Inventors: Carl Lance Boling, San Jose, CA (US); Benjamin David Pless, Atherton, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 457 days.

(21) Appl. No.: 14/320,107

(22) Filed: Jun. 30, 2014

(65) Prior Publication Data

US 2015/0005858 A1    Jan. 1, 2015

Related U.S. Application Data (60) Provisional application No. 61/840,485, filed on Jun. 28, 2013.

(51) Int. Cl.
*C04B 41/00* (2006.01)
*B23K 26/60* (2014.01)
(Continued)

(52) U.S. Cl.
CPC .......... *A61N 1/375* (2013.01); *B23K 26/0006* (2013.01); *B23K 26/0066* (2013.01);
(Continued)

(58) Field of Classification Search
CPC ........ A61N 1/375; B23K 26/60; B23K 26/12; C04B 41/0036
(Continued)

(56) References Cited

U.S. PATENT DOCUMENTS

| 2,537,068 A | 1/1951 | Lilliendahl et al. |
| 4,879,450 A | 11/1989 | Valentin et al. |

(Continued)

FOREIGN PATENT DOCUMENTS

| DE | 19848179 A1 | 5/2000 |
| WO | 2013074755 A1 | 5/2013 |

OTHER PUBLICATIONS

Eshed et al. Zirconium nanoparticles prepared by the reduction of zirconium oxide using the RAPET method. Beilstein Journal of Nanotechnology. vol. 2. 2011 pp. 198-203.*

(Continued)

*Primary Examiner* — Cachet Sellman
(74) *Attorney, Agent, or Firm* — Tarolli, Sundheim, Covell & Tummino LLP (57) ABSTRACT

Various methods for laser welding biocompatible material for use in implantable medical devices are disclosed. A method for laser processing includes applying a laser beam to a biocompatible material comprising at least 85% by weight zirconium oxide ($ZrO_2$) or "zirconia" in an oxygen-free environment and depleting the material of oxygen. The depletion of oxygen converts the zirconium oxide to elemental zirconium at an interface where the material is applied to the elemental zirconium. In one embodiment, the present invention provides for an implantable medical device or component thereof made of a biocompatible material comprising zirconium oxide. The device includes a substrate that has an intrinsic conductive pathway comprising elemental zirconium that extends from a first surface to a second surface of the substrate.

17 Claims, 7 Drawing Sheets

(51) Int. Cl.
  *A61N 1/375* (2006.01)
  *B23K 26/00* (2014.01)
  *B23K 26/12* (2014.01)
  *C04B 41/80* (2006.01)
  *B23K 26/32* (2014.01)
  *C04B 111/00* (2006.01)
  *B23K 103/00* (2006.01)

(52) U.S. Cl.
  CPC ............ *B23K 26/123* (2013.01); *B23K 26/32* (2013.01); *B23K 26/60* (2015.10); *C04B 41/009* (2013.01); *C04B 41/0036* (2013.01); *C04B 41/80* (2013.01); *B23K 2203/52* (2015.10); *C04B 2111/00836* (2013.01)

(58) Field of Classification Search
  USPC .......................... 427/2.1–2.31, 554; 607/116
  See application file for complete search history.

(56) References Cited

U.S. PATENT DOCUMENTS

| | | | |
|---|---|---|---|
| 5,272,120 A * | 12/1993 | Kosuda | G01B 3/30 219/121.6 |
| 5,543,269 A * | 8/1996 | Chatterjee | B41M 5/262 430/346 |
| 5,804,342 A | 9/1998 | Paz-Pujalt et al. | |
| 6,232,004 B1 * | 5/2001 | Lasater | C04B 41/5133 427/190 |
| 6,420,305 B1 * | 7/2002 | Matsuzawa | B01J 21/066 502/222 |
| 6,869,701 B1 * | 3/2005 | Aita | A61L 27/306 428/336 |
| 8,494,641 B2 | 7/2013 | Boling et al. | |
| 2003/0087197 A1 * | 5/2003 | Schulman | C23C 14/042 430/315 |
| 2007/0137734 A1 * | 6/2007 | Pawar | A61F 2/30767 148/206 |
| 2009/0030515 A1 * | 1/2009 | Schuessler | A61F 2/12 623/8 |
| 2010/0174383 A1 * | 7/2010 | Pawar | A61F 2/30767 623/23.56 |
| 2010/0268337 A1 * | 10/2010 | Gordon | A61F 2/28 623/16.11 |
| 2012/0097653 A1 * | 4/2012 | Yabe | C01B 33/023 219/121.85 |
| 2013/0034665 A1 * | 2/2013 | Yilbas | C04B 41/87 427/554 |

OTHER PUBLICATIONS

PCT International Search Report and Written Opinion for PCT/US2014/044929, mailed Feb. 2, 2015, pp. 1-18.

* cited by examiner

IMPLANTABLE MEDICAL DEVICE AND METHOD FOR LASER PROCESSING

RELATED APPLICATION

This patent application claims priority to Application Ser. No. 61/840,485 entitled "Method For Laser Welding Zirconium Oxide For Use in an Implantable Medical Device" filed on Jun. 28, 2013, the entirety of which is incorporated by reference herein.

TECHNICAL FIELD

Embodiments of the present invention relate generally to implantable medical devices and methods for laser processing the devices. More specifically, the present invention relates to implantable medical devices and methods for laser processing biocompatible material comprising zirconium oxide.

BACKGROUND OF THE INVENTION

Electrical stimulation of peripheral, central and autonomic neural structures have shown increased interest due to the potential benefits it may provide to individuals suffering from many neurological and behavioral diseases. Many of these therapies today are not well accepted or are considered last in the therapeutic options due to the invasive nature of the therapy even through the efficacy may be quite good. This has created a need for less invasive therapies that are directed toward patient and physician clinical needs Implantable neurostimulator devices are used to deliver therapy to patients to treat a variety of symptoms or conditions such as chronic pain, tremor, Parkinson's disease, epilepsy, incontinence, sexual dysfunction, or gastroparesis. The neurostimulator delivers neurostimulation therapy via one or more leads that include electrodes located proximate to the peripheral, central or autonomic neural structures of a patient. In general, the neurostimulator delivers neurostimulation therapy in the form of electrical pulses. Depending on the application for which they are implanted in a patient, neurostimulators may include a variety of electrical and/or mechanical components. Typically, a neurostimulator includes a rigid hermetically electronics enclosure that houses all of its components, which are generally fragile, to protect the components from forces to which they would otherwise be exposed when implanted within the human body. The size and shape of a neurostimulator housing is dependent on the sizes and shapes of the components of the neurostimulator.

Typically implantable medical devices are hermetically sealed by first using a brazing process between a ceramic (e.g. partially stabilized zirconium oxide) and a metal (e.g. titanium) to create a zirconium oxide to metal bond. The final seal is made by laser welding a titanium lid to the metal component. Some neurostimulators communicate wireless via radio frequency therefore using a welding method that eliminates the metal components (e.g. titanium) would be advantageous and increase communication performance.

SUMMARY OF THE INVENTION

In one aspect of the present invention, a method for laser processing includes applying a laser beam to a biocompatible material of an implantable medical device in an oxygen-free environment and depleting the material of oxygen. The biocompatible material comprises at least about 50% zirconium oxide and the depletion of oxygen converts the zirconium oxide to elemental zirconium at an interface where the laser beam is applied to the material. In one example embodiment the method of laser processing creates conductive circuitry of elemental zirconium in the biocompatible material comprising zirconium oxide. In another example embodiment the method of laser processing creates an intrinsic conductive pathway in the biocompatible material comprising zirconium oxide.

In another aspect of the present invention, a method for laser processing includes applying a laser beam near two opposing surfaces of biocompatible material comprising zirconium oxide. The laser pulses are applied in an oxygen-free environment thus depleting the zirconium oxide of oxygen. The zirconium oxide is converted to elemental zirconium and the two surfaces of elemental zirconium join.

In yet another embodiment, the present invention provides for an implantable medical device, or component thereof, of a biocompatible material comprising zirconium oxide and an intrinsic conductive pathway of elemental zirconium that extends from a first surface to a second surface of the device or component. The presence of zirconium provides a conductive pathway that is intrinsic to an otherwise non-conductive device.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Various embodiments of the present invention are provided and relates generally to laser processing material comprising zirconium oxide ($ZrO_2$), commonly known as zirconia, for use in an implantable medical devices. More specifically, various embodiments of the present invention relate to laser welding material containing zirconium oxide to improve performance of the implantable medical device. Although several embodiments of the present invention described herein relate to specific implantable devices and components of the devices illustrated herein, it should be understood that the teachings and concepts herein apply to devices comprising biocompatible materials that include zirconium oxide.

Unless otherwise defined, all technical terms used herein have the same meaning as commonly understood by one of ordinary skill in the art to which the present disclosure pertains.

As used herein, the term "biocompatible material" can be an organic material or an inorganic material that elicits little or no immune response in a patient's body.

As used herein, the term "oxygen-free environment" refers to an environment which has a low, or near-zero, oxygen content. Examples of oxygen-free environment include an environment having less than 300 ppm oxygen, or an anaerobic (i.e. without air) environment, for example. Oxygen-free environments can further include a reducing environment, an inert environment, or a combination of a reducing and inert environment. It should be understood that in the context of the embodiments of laser processing described herein that an oxygen-free environment can have a level of oxygen that is capable of reducing the biocompatible material containing zirconium oxide to elemental zirconia at an interface of the material exposed to laser light beam.

As used herein and in the appended claims, the singular forms "a", "and", and "the" include plural referents unless the context clearly dictates otherwise.

Unless otherwise indicated, all numbers expressing quantities used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

Figure 1:
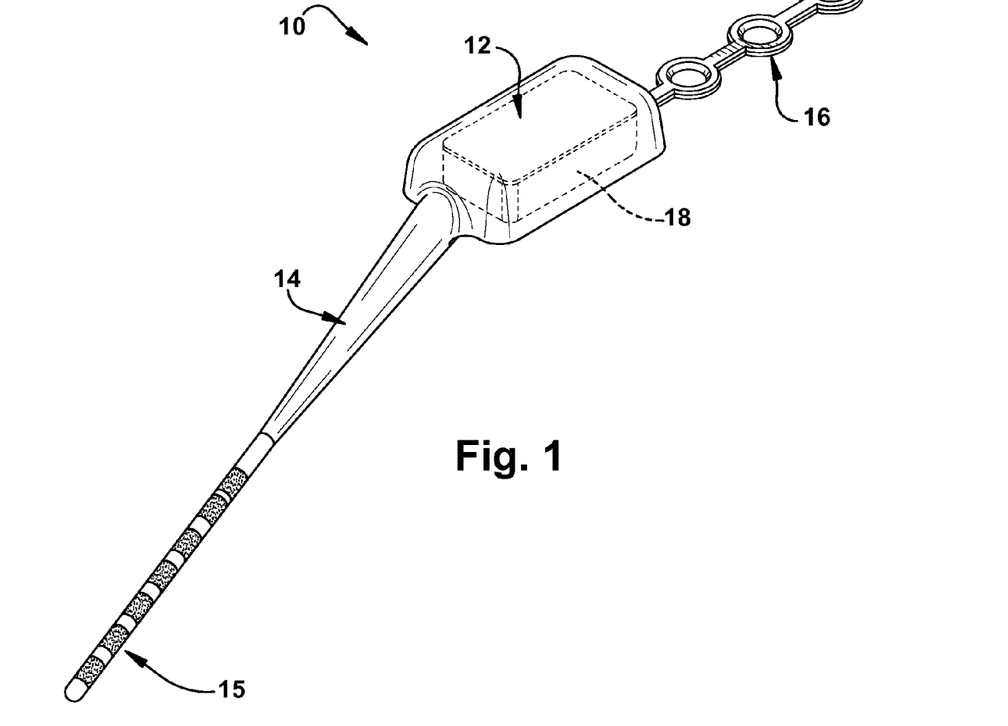
FIG. 1 is a perspective view of an implantable neurostimulator unit, according to an embodiment of the present invention.

Aspects of the present invention can be described with respect to FIG. 1 which is a perspective view illustration of an implantable neurostimulator unit 10. As mentioned above, it should be understood that implantable neurostimulator unit 10 and related components are just one example of a myriad of possible implantable medical devices that can be manufactured and used in accordance with the embodiments of the present invention. Neurostimulator unit 10 includes a stimulator body 12, an integral stimulator lead 14 having one or more stimulating electrodes 15, and an integral fixation apparatus 16 that is used to attach the unit to the patient. The stimulator body 12 includes electronics enclosure 18 (shown in phantom). Neurostimulator 10 and related components are made of biocompatible materials. For example, electronics enclosures such as electronic enclosure 18 is made of a non-conductive material such as ceramic materials which generally include, aluminum oxide, zirconium oxide, aluminum nitride, and glass. In other applications conductive electronic enclosure contain circuit assemblies that are photo etched onto organic substrates.

In some instances, neurostimulator unit 10 can be of the type disclosed in U.S. Pat. No. 8,494,641 (hereinafter, "the '641 patent"), the entirety of which is hereby incorporated by reference herein. A neurostimulator unit can generally include any active implantable medical device configured to deliver electrical stimulation, alone or in combination with other types of stimulation to tissue of a subject. The neurostimulator can further include any active implantable medical device configured for implantation for a relatively short period of time (e.g., to address acute medical conditions) or a relatively long period of time (e.g., to address chronic medical conditions). Additionally, the neurostimulator can include one or more elements used to record or monitor a physiological response of a subject's tissue (e.g., a delivered therapy), as well as one or more other components that interface with the patient's tissue (e.g., therapeutic agent delivery mechanisms, sensors, etc.).

Several advantages in manufacturing and product performance are realized with the methods of laser processing described herein. Laser processing, such as for example, laser welding of material containing zirconium oxide is found to improve both the manufacture and performance of an implantable neurostimulator used to deliver electrical stimulation to a peripheral, central or autonomic neural structure.

Figure 2:
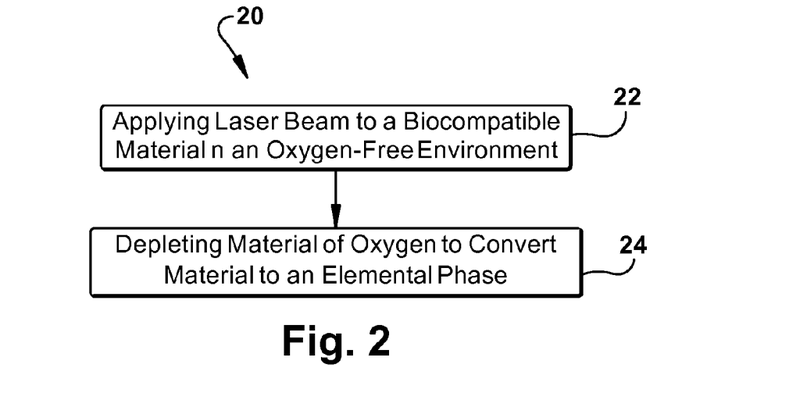
FIG. 2 is a flow diagram illustrating a method for laser processing biocompatible material of an implantable medical device, according to an embodiment of the present invention.

With reference to FIG. 2 a flow scheme 20 for various methods of laser processing components of an implantable medical device, for example, neurostimulator unit 10, is described. In one flow scheme, the method of laser processing starts at box 22 which depicts the step of applying a laser beam to a biocompatible material comprising zirconium oxide in an oxygen-free environment, and at box 24 the method depicts the step of depleting oxygen from the biocompatible material, zirconium oxide (ZrO2) or "zirconia" to convert a layer of the material to elemental zirconium. The layer of elemental zirconium is formed at the interface portion of the biocompatible material exposed to the laser beam which converts to elemental zirconium. The method steps 22 and 24 can be an integral step, as the material can be depleted of oxygen instantaneously and/or simultaneously while the laser beam is applied in an oxygen-free environment.

As described above, an oxygen-free environment can be achieved in several different ways. For example the environment that contacts the biocompatible material exposed to the laser beam can be a reducing environment or an inert environment or an environment with a mixture of reducing and inert mediums. The shielding gas prevents the ingress of oxygen to the biocompatible material comprising zirconium oxide. The oxygen-free environment can be achieved by placing the medical device in a chamber with shielding gas where it is exposed to laser light. Alternatively, the medical device can be flooded with shielding gas during the laser operation. As another example, a vacuum can be applied during the laser operation. The oxygen-free environment can comprise several possible compositions of fluid medium, including but not limited to, argon, helium, carbon dioxide, hydrogen, and nitrogen gases and mixtures thereof.

In accordance with the laser processing methods described herein, the biocompatible material of the medical device or component comprises, by weight, at least about 50% zirconium oxide ($ZrO_2$), in another embodiment from about 75% to about 99%, in another embodiment from about 85% to about 99%, in another embodiment from about 95% to about 99%. The balance of the biocompatible material can include a variety of other substances, for example other oxides and the presence of impurities. Other oxides can include, but are not limited to, aluminum oxide, silicon oxide, calcium oxide, iron oxide, sodium oxide, potassium oxide, yttrium oxide, hafnium oxide, and alloys thereof, for example.

In another example embodiment, the biocompatible material comprises, by weight, from about 90% to about 99% zirconium oxide and from about 1% to about 10% yttrium and/or yttrium oxide (Y2O3), and in another embodiment from about 95% to 99% zirconium oxide from about 1% to about 5% yttrium and/or yttrium oxide (Y2O3), and. A high-purity material that is approved for use in biological applications and used in surgical implant applications is yttria-stabliized tetragonal zirconia polycrystal (Y-TZP) which comprises at least 99% by weight Zirconium oxide/ Hafnium Oxide plus yttrium oxide (ZrO2HfO2+Y2O3). Commercially available products of yttria-stabliized tetragonal zirconia polycrystal (Y-TZP) include about 2.5% to about 5.4% by weight yttrium oxide (Y2O3) and less than 5% by weight hafnium oxide (HfO2). High purity Yttria-stabliized tetragonal zirconia polycrystal (Y-TZP) is available from C5 MedicalWerks, Kyocera, Morgan Technical Ceramics of Grand Junction, Colo.

Lasers that can be used in the methods of laser processing biocompatible materials are commercially available and include, but are not limited to, solid-state lasers such as Nd:YAG (neodymium-doped yttrium aluminium garnet) lasers, and gas lasers such as carbon dioxide CO2 gas lasers. Lasers can operate in either or both of the pulse and continuous modes. Nd:YAG lasers typically emit light with a wavelength of 1064 nm in the infrared but high intensity pulsed may be frequency doubled to generate laser light at 532 nm or higher harmonics. As appreciated by those skilled in the art, care must be taken during laser processing to avoid conditions which are either too benign or too severe. Laser processing conditions which are too benign, i.e. insufficient in time or intensity, can result production of products which lack desired properties. For example in the methods for laser processing described herein, the intensity can range from about 0.1 Joules to about 50 Joules, in another embodiment, from about 0.5 Joules to about 30 Joules. Elemental zirconium melts at approximately 1850° C., much lower than the melting temperature of zirconium oxide which melts at approximately 2700° C., and so the laser is applied such that the temperature of the biocompatible material interface is heated to slightly less than the melting point of zirconium.

In another embodiment the process described above with respect to FIG. 2 further includes preheating the biocompatible material prior to applying the laser beam to the substrate of the biocompatible material. The preheat temperature of the biocompatible material can vary depending upon the application, however, in one example embodiment, the biocompatible material can be preheated to less than the melting temperature of zirconium or less than about 1850° C.

As noted above with respect to FIG. 1, the microelectronics of neurostimulator unit 10 can be housed in an electronics enclosure 18 which located inside stimulator body 12. The electronics enclosure 18 is a hermetic enclosure that protects the microelectronics from fluid ingress when implanted within the body. The electronics enclosure 18 can include a variety of microelectronics assemblies including, but not limited to, circuit cards (FIG. 6), a feed-through assembly (FIG. 9), and a lead interconnect assembly (not shown), and the stimulator body 12 can be molded with a protective outer layer. In some embodiments the dimensions of the stimulator body are 8 mm wide, 4 mm thick, and 14 mm long, for example.

Figure 3:
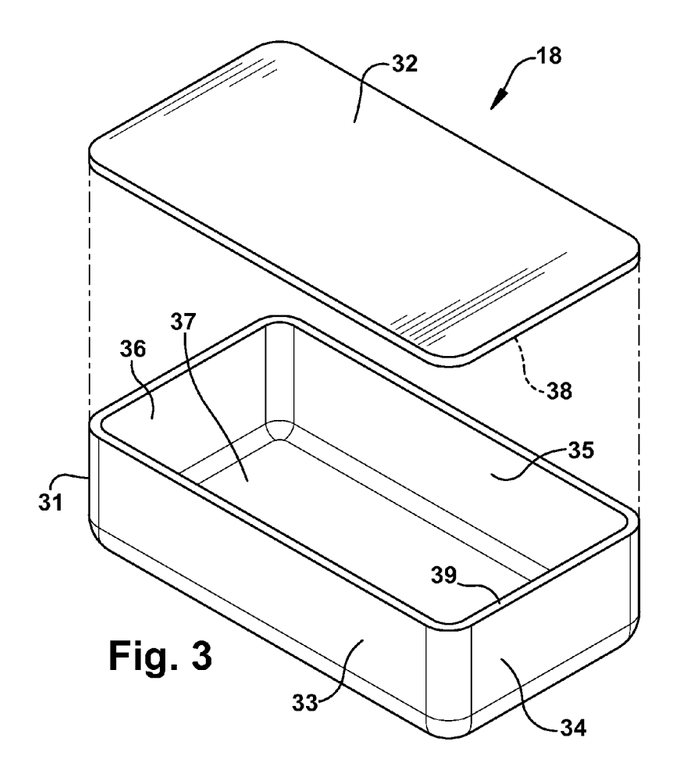
FIG. 3 is a perspective view of an electronics enclosure for an implantable neurostimulator unit shown in an open position, according to an embodiment of the present invention.

FIG. 3 is a perspective view of electronics enclosure 18 shown in an open position prior to the placement of microelectronic components. In accordance with an embodiment of the present invention, electronics enclosure 18 includes base 31 and lid 32. Base 31 has sidewalls 33, 34, 35, 36 and bottom wall 37. Lid 32 can be dimensioned the same as the perimeter of base 31 so that bottom surface 38 of lid 32 rests on top edge 39 of sidewalls and is flush with sidewalls, although other dimensions are possible.

Figure 4:
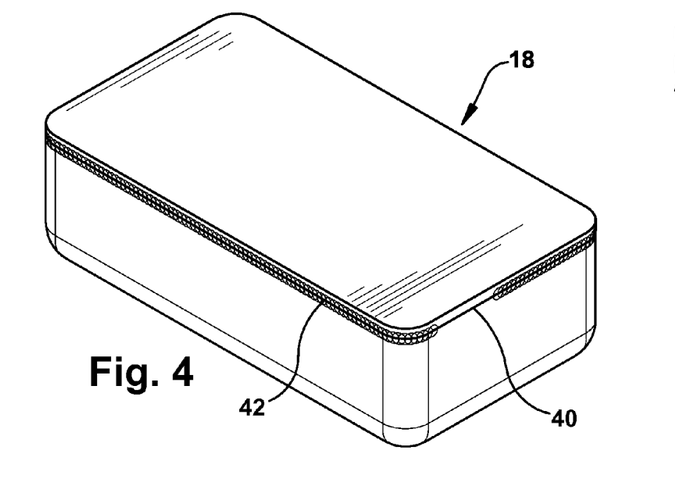
FIG. 4 is a perspective view of an electronics enclosure for an implantable neurostimulator unit shown in the closed and sealed position, according to an embodiment of the present invention.

FIG. 4 is a perspective view of electronics enclosure of FIG. 3 in the closed and hermetically sealed position. The opposing surfaces of internal edge 38 of lid 32 and top edge 38 of base 31 are in contact with one another along the perimeter of the electronics enclosure 18 at interface 40. Laser weld 42 is formed by the method of laser processing described herein.

In one embodiment of the present invention, the base 31 and lid 32 are each biocompatible materials comprising, by weight, at least 50% zirconium oxide, in another embodiment from about 85% to about 99%, in another embodiment from about 90% to about 99%, and in another embodiment from about 95% to about 99% zirconium oxide. The composition of base 31 and lid 32 can be the same or different. The composition of biocompatible material of the base and lid can also include, by weight, from about 1% to about 10% yttrium. As mentioned above, a high-purity material that is approved for use in biological applications and used in surgical implant applications is yttria-stabliized tetragonal zirconia polycrystal (Y-TZP) which comprises at least 99% by weight Zirconium oxide/Hafnium Oxide plus yttrium oxide ($Zr_{O2}Hf_{O2}+_{Y2O3}$).

Figure 5:
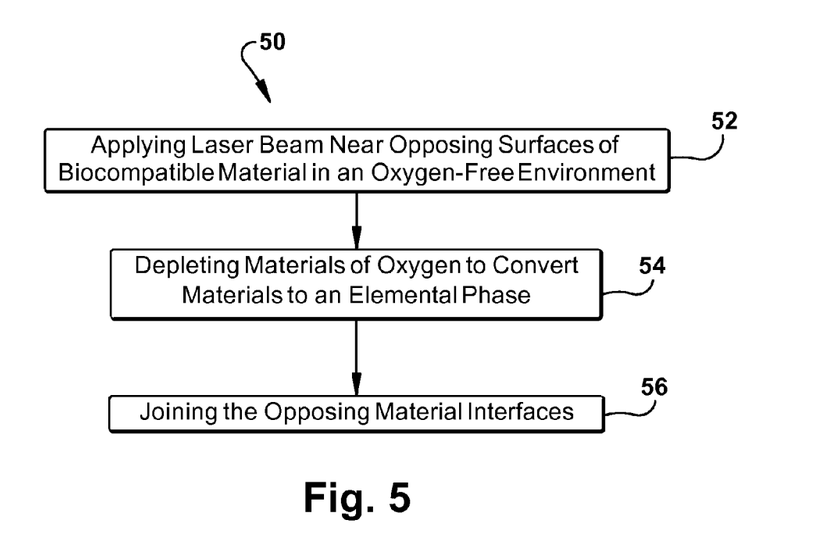
FIG. 5 is a flow diagram illustrating a method for laser processing an implantable medical device, according to an alternative embodiment of the present invention.

FIG. 5 is a flow schematic 50 illustrating a method for laser processing an implantable processing biocompatible material to create a hermetic seal. In one flow scheme, the method of laser processing starts at box 52 which depicts the step of applying a laser beam near opposing surfaces of biocompatible material where at least one opposing surface comprising zirconium oxide in an oxygen-free environment. Box 54 depicts the step of applying the laser while depleting oxygen from the biocompatible material, zirconium oxide or "zirconia" to convert the interface of the material to a layer of elemental zirconium. The interface is the portion of the biocompatible material exposed to the laser beam and which converts to elemental zirconium. As described above with respect to FIG. 2, the method steps 52 and 54 can be an integral step, as the material can be depleted of oxygen instantaneously and/or simultaneously while the laser beam is applied in an oxygen-free environment. Box 56 depicts the step of joining the opposing material surfaces. If the opposing surfaces are in physical contact or communication, the joining is automatic as the two materials will bond and join.

Figure 4A:
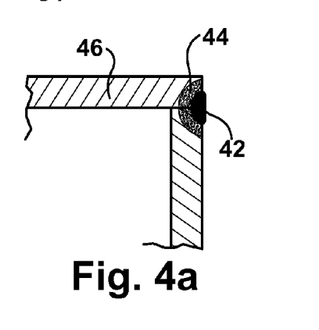
FIG. 4a is a cross-sectional view of the hermetically sealed electronics enclosure of FIG. 4.

Referring back to FIG. 4 the resulting weld 42 of the process described in FIG. 5 hermetically seals electronics enclosure 18 along the top edge of sidewalls 33, 34, 35, and 36. FIG. 4a is a cross-sectional illustration of the laser weld of FIG. 4 showing weld 42 comprising elemental zirconium, a laser-affected-zone (LAZ) 44, and the bulk material 46 comprising zirconium oxide. The laser-affected-zone can have a different morphology and/or composition of than either weld 42 or bulk material 46 and can comprise both zirconium oxide and zirconium.

Thus, in one embodiment the laser beam is applied to biocompatible material that is two separate components of the electronics enclosure in contact with one another, that is, such that the base and lid are in contact with one another while the laser is applied in an oxygen-free environment. The biocompatible material comprising zirconium oxide converts to elemental zirconium at the opposing surfaces in physical communication with one another and the surfaces fuse together as a hermetic weld.

In another embodiment the opposing surfaces, for example the base and lid, can be separated from one another and the method includes applying the laser beam between or near the opposing surfaces of both base and lid such that the heat energy of the laser depletes the oxygen of zirconium oxide converting the surface of lid and surface of base to elemental zirconium at the interfaces of laser beam exposure in an oxygen-free environment, and placing the base and lid in contact with one another so that the elemental zirconium from each component fuse together.

In the example method embodiments described above for hermetically sealing electronic enclosure 18 of via laser welding, a glove box could be used to control the atmosphere around the substrate, a vacuum could be applied, or the electronic enclosure could be flooded with a reducing or inert gas or combination of a reducing and inert environment. In such case, an amount of gas sufficient to eliminate the ingress of oxygen to the component surface of the electronic enclosure or other implantable medical device is used.

Accordingly, the methods of laser processing described herein result in a hermetically sealed medical device having a flow rate of less than $1 \times 10^{-9}$ atm.cc/s of helium or otherwise in accordance with at least one of the hermetic standards, for example, Mil-std-883, BS9000, IEC749 or Mil 202F.

In alternative embodiment of the present invention, the above methods of laser processing further include preheating or post-cooling or both. The method can include preheating the biocompatible material prior to applying the laser beam to the substrate of the biocompatible material. The preheat temperature of the biocompatible material can vary depending upon the application. In another embodiment the material interfaces are optionally include cooling the medical device including the interface at which the laser beam is applied after applying the laser beam. Cooling is carried out at a controlled rate that prevents cracking of the biocompatible material in the laser affected zone (LAZ). The cooling rate depends upon at least the size and geometry of the component and composition of the biocompatible material. For example the component can be cooled at a rate of 5 to 10 degrees per minute, although cooling rate can vary widely.

In conventional applications, some implantable medical devices, such as neurostimulator 10 communicate and receive power wirelessly via radio frequency (RF) therefore having a bezel and lid made from metal (e.g. titanium) can reduce the efficiency and performance of RF communication. The inventive embodiments of implantable devices herein made with laser processing as described herein are advantageous because both lid and base could be made of zirconium oxide and welded together via the inventive method thus eliminating the metal component. The medical device comprising zirconium oxide/zirconium, in accordance with the embodiments of the present invention are radio transparent. In addition, conventional methods of making electronic enclosures require more components, such as a bezel that is brazed at high temperatures for a gas-tight seal between the bezel and the ceramic substrate of the electronics enclosure. In conventional processes a titanium bezel or rim is brazed around the zirconium oxide housing at high temperatures. This is done by depositing a thin film of titanium onto the rim of the zirconium oxide, followed by depositing a thin film of platinum on the same surface of the zirconium oxide electronics enclosure, and then applying a gold pre-formed ring where the titanium bezel and zirconium oxide shall interface. The assembly is brazed at high temperature and the result is an open electronics enclosure with a metal rim or bezel. A flat titanium lid is then applied to the bezel and laser welded. Thus, the methods described herein eliminate the thin film metal deposition process as well as the bezel component.

In alternative embodiments of the present invention, the lid can be a different material than the base and laser processed according to the methods described above in an oxygen-free environment. In an example embodiment, the lid can be a high resistance, biocompatible metal such as commercially pure or alloyed titanium and the base is a biocompatible material comprising, zirconium oxide as described above, for example, by weight, at least about 50%, in another embodiment from about 75% to about 99%, and alternatively, from about 95% to about 99% by weight zirconium oxide.

Figure 6:
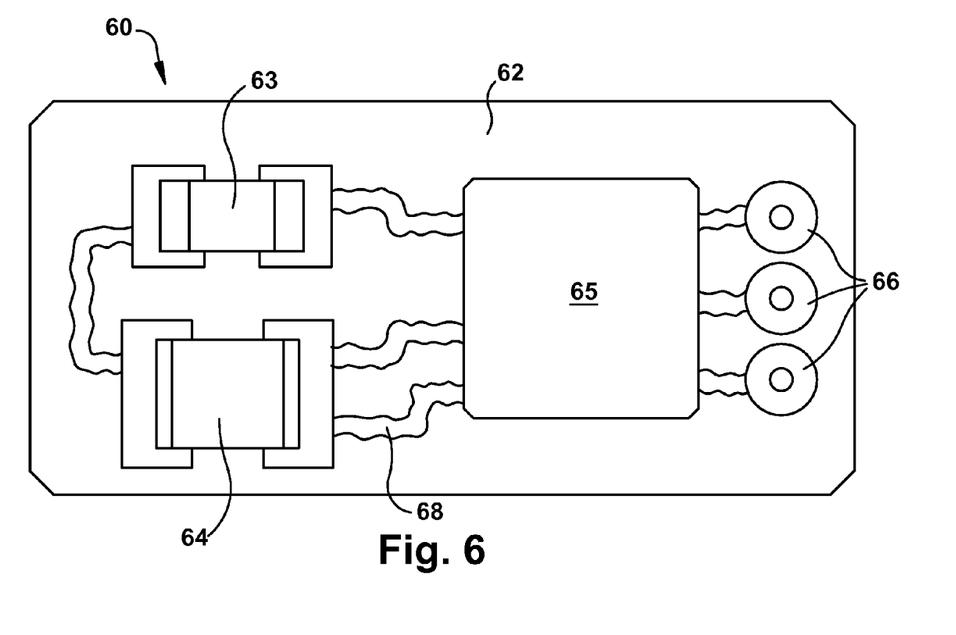
FIG. 6 is a top view of a circuit card, according to an embodiment of the present invention.

FIG. 6 is a top view of a circuit card 60 that can be placed into or integrated as a portion of the implantable neurostimulator unit 10, according to an embodiment of the present invention. Circuit card 60 includes substrate 62 which is a biocompatible material comprising zirconium oxide, electrical components, for example, passive components 63 and 64, ASIC BEA 65, and metallized annular rings 66. Circuit card 60 also includes a plurality of conductive traces 68 comprising elemental zirconium, made in accordance to the various methods of laser processing described herein. The conductive traces 68 may be of conductive value, or resistive value, or be of variable resistance to control electron flow. For example, if the metal trace is wide it will be more conductive and if there is a case in which the electrical circuit might need a higher resistance conductor between two said components, the conductive trace can be made to be thinner in width such that the resistance can be increased without having a separate passive resister. The thickness of the layer of elemental zirconium formed therein can vary, for example from about three hundred angstroms to about 0.05 inches, for example, and depending upon the application.

Figure 7:
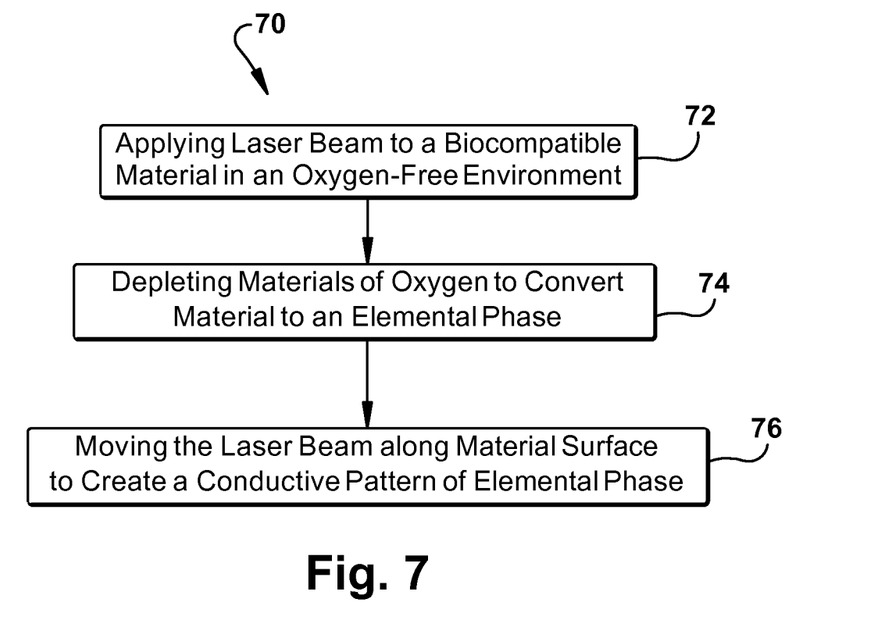
FIG. 7 is a flow diagram illustrating a method for laser processing an implantable medical device, according to an alternative embodiment of the present invention.

FIG. 7 is a flow diagram illustrating a method for laser processing an implantable medical device, according to an alternative embodiment of the present invention. FIG. 7 depicts a flow scheme 70 of a method for creating a pattern of traces for electronic circuitry on a biocompatible material of an implantable medical device. In one embodiment, the method of laser processing starts at box 72 which depicts the step of applying a laser beam to a biocompatible material comprising zirconium oxide in an oxygen-free environment, and at box 74 the method depicts the step of applying the laser while depleting oxygen from the biocompatible material, zirconium oxide or "zirconia" to convert the interface of the material to elemental zirconium. The interface is the portion of the biocompatible material exposed to the laser beam and converts to elemental zirconium. At box 76 the method includes moving the laser beam along the material surface to create a pattern or trace of elemental zirconium. The trace is formed as the oxygen is consumed by the heat of the laser, creating the zirconium. The oxygen-free environment can comprise several possible compositions of fluid medium, including but not limited to, argon, helium, carbon dioxide, hydrogen, and nitrogen gases and mixtures thereof.

As describe with the methods of laser processing above the biocompatible material of the medical device or component comprises, by weight, at least about 50% zirconium oxide ($ZrO_2$), in another embodiment from about 75% to about 99%, in another embodiment from about 85% to about 99%, in another embodiment from about 95% to about 99%. The balance of the biocompatible material can include a variety of other substances, for example other oxides and the presence of impurities described above.

Advantageously, the above method of laser processing described above allows metal circuitry to be created directly on an implantable medical device, such as circuit card 60 (FIG. 6) which can be placed inside electronics enclosure 18 or directly on the base 32 of electronics enclosure of neurostimulator unit 10. This greatly simplifies the assembly process. Using this metal circuitry also allows the ability to take advantage of additional space within the electronics enclosure so that circuits can be run on all available surfaces including the side walls of the enclosure. Also, using simple resistor circuits can be created directly on the enclosure surface, thus eliminating the need for bulky passive components.

In an alternative embodiment the method 70 for laser processing further includes pre-heating the biocompatible material prior to applying the laser beam. In yet another embodiment the method further includes post-cooling the biocompatible material at a controlled rate as described above.

Figure 8:
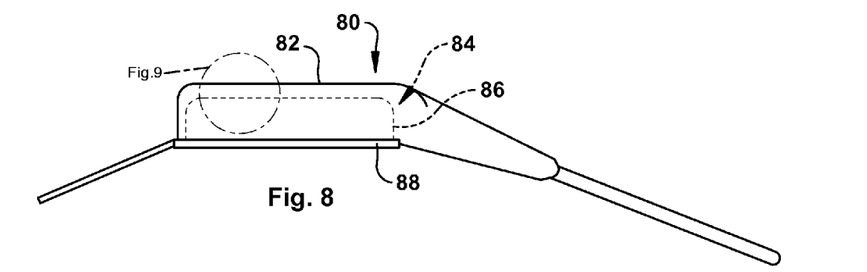
FIG. 8 is a side view of the implantable neurostimulator unit of FIG. 1 showing an electronics enclosure in phantom, according to an embodiment of the present invention.
Figure 9:
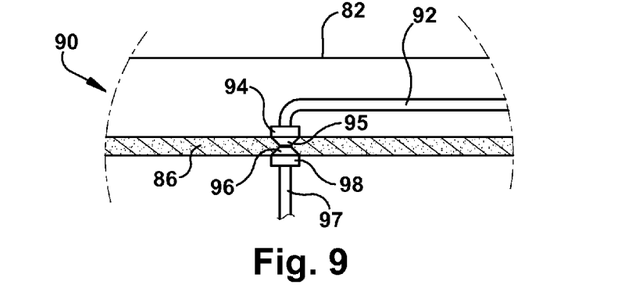
FIG. 9 is a side-view of an electronics enclosure showing a feedthrough assembly, according to an embodiment of the present invention.

FIG. 8 is a side view of the implantable neurostimulator unit 80 of FIG. 1 showing neurostimulator housing 82 and an electronics enclosure 84 (in phantom) therein, according to an embodiment of the present invention. Electronics enclosure 84 includes substrates 86 and 88. FIG. 9 is a close-up cross-section of electronics enclosure 84 of FIG. 8 showing a feedthrough assembly 90. Feedthrough assemblies are used in electronic systems to carry a signal through a non-conductive or semi-conductive enclosure or printed circuit card. Feedthrough assembly 90 includes conductor wires 92, 97 used to connect to top and bottom surfaces of base 86 to carry a signal through an enclosure 84. Ferrules, or heads of the conductor wires, 94 and 98 are attached to the enclosure via several possible methods, for example, via a conductive epoxy, an ultrasonic weld, a laser weld, etc. Conductor 92 is the wire outboard and provides the conductive path to the neural anatomy, and conductor 97 connects to the electronics. Intrinsic conductive pathways 95 and 96 are the laser converted conductive elements, for example intrinsic conductive pathways comprising zirconium, and intrinsic pathways 95 and 96 are in contact with conductor 92 and 97 and together make up the feedthrough assembly 90.

Figure 10:
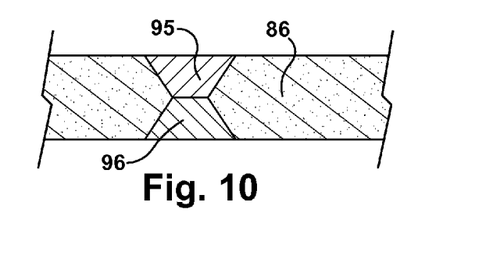
FIG. 10 is a close-up view of a base of the electronics enclosure of FIG. 9 with an intrinsic conductive pathway, according to an embodiment of the present invention.

FIG. 10 is a close up view of the intrinsic pathway 95, 96 which is an intrinsic conductive pathway that is incorporated or intrinsic in the base 86 of electronics enclosure. Conductors 92, 97 are typically made of an insulating material that surrounds a conductive wire that provides circuit communication. The feedthrough assembly can be an RF-feedthrough which is specifically designed to carry very high frequency RF or microwave electrical signals. In one embodiment, the inventive implantable component, such as base 84 herein comprises zirconium oxide and includes an intrinsic conductive pathway comprising elemental zirconium that extends from a first surface to a second surface of the electronics enclosure. The zirconium intrinsic pathway creates a conductive pathway that is intrinsic to zirconium oxide base that makes up the electronics enclosure. There is no need for an opening in the enclosure to feed the wires and there is no need for brazing.

Figure 11:
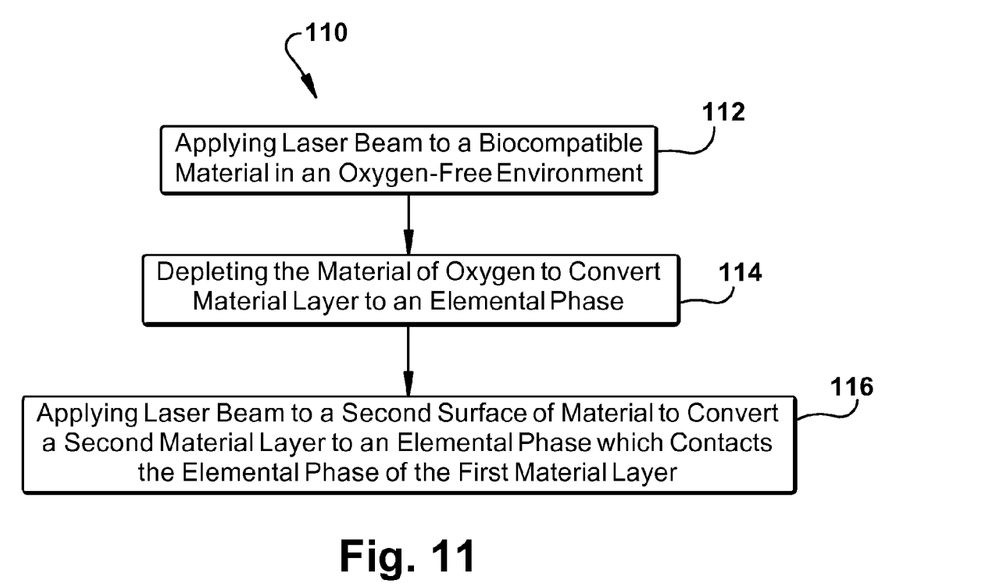
FIG. 11 is a flow diagram illustrating a method for laser processing an implantable medical device with feedthrough, according to an alternative embodiment of the present invention.

FIG. 11 is a flow diagram illustrating a method 110 for laser processing an implantable medical device according to an alternative embodiment of the present invention. In one embodiment, the method of laser processing starts at box 112 which depicts the step of applying a laser beam to a biocompatible material comprising zirconium oxide in an oxygen-free environment, and at box 114 the method depicts the step of applying the laser while depleting oxygen from the biocompatible material, zirconium oxide or "zirconia" to convert the interface of the material to elemental zirconium. The interface is the portion of the biocompatible material exposed to the laser beam and converts to elemental zirconium. At box 116 the method includes applying a laser beam to a second surface of material to convert a second material layer to an elemental phase which contacts the elemental phase of the first material layer. As shown above in FIG. 10 the elemental phase layer created in the second surface 96 and contacts the elemental phase layer created in the first surface 95 to form the intrinsic conductive pathway. The layer of elemental phase comprises zirconium and is formed as the oxygen is consumed by the heat of the laser, creating the zirconium. As mentioned above the oxygen-free environment can be a reducing or inert atmosphere, or combination thereof, and can comprise several possible compositions of fluid medium, including but not limited to, argon, helium, carbon dioxide, hydrogen, and nitrogen gases and mixtures thereof.

As describe with the methods of laser processing above the biocompatible material of the medical device or component comprises, by weight, at least about 50% zirconium oxide ($ZrO_2$), in another embodiment from about 75% to about 99%, in another embodiment from about 85% to about 99%, in another embodiment from about 95% to about 99%. The balance of the biocompatible material can include a variety of other substances, for example other oxides and the presence of impurities described above.

Figure 12:
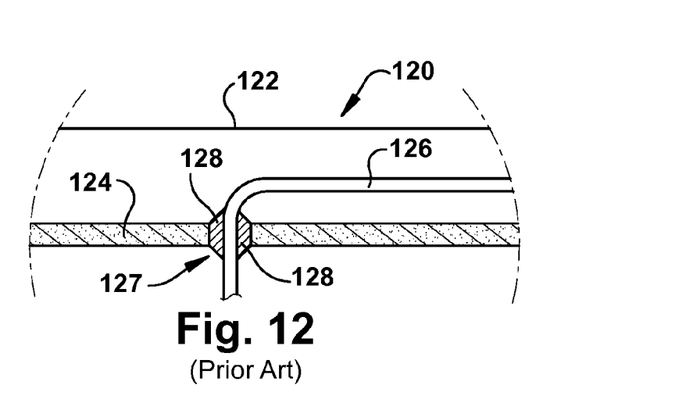
FIG. 12 is a view of the prior art showing a conventional feedthrough assembly, in accordance with the prior art.

FIG. 12 is a view of the prior art showing a conventional feedthrough assembly, in accordance with the prior art. The enclosure 120 comprises a lid 122, a substrate 124 and a feedthrough wire 126. The substrate is manufactured from stabilized zirconium oxide and the feed-through wire is gold brazed into place with a brazing compound 128 and manufactured from platinum-iridium 80/20, 90/10 or pure platinum. The lid is typically manufactured using a high resistance, biocompatible metal such as commercially pure or alloyed titanium.

By contrast, the an embodiment of the present invention provides for an implantable medical device, or component thereof, as illustrated in FIGS. 8-10, of a biocompatible material comprising zirconium oxide and an intrinsic conductive pathway of elemental zirconium that extends from a first surface to a second surface of the device or component. The presence of zirconium provides a conductive pathway that is intrinsic to an otherwise non-conductive, or semi-conductive device.

EXAMPLES

The following Example is provided to more thoroughly illustrate embodiments of the present invention.

Figure 13:
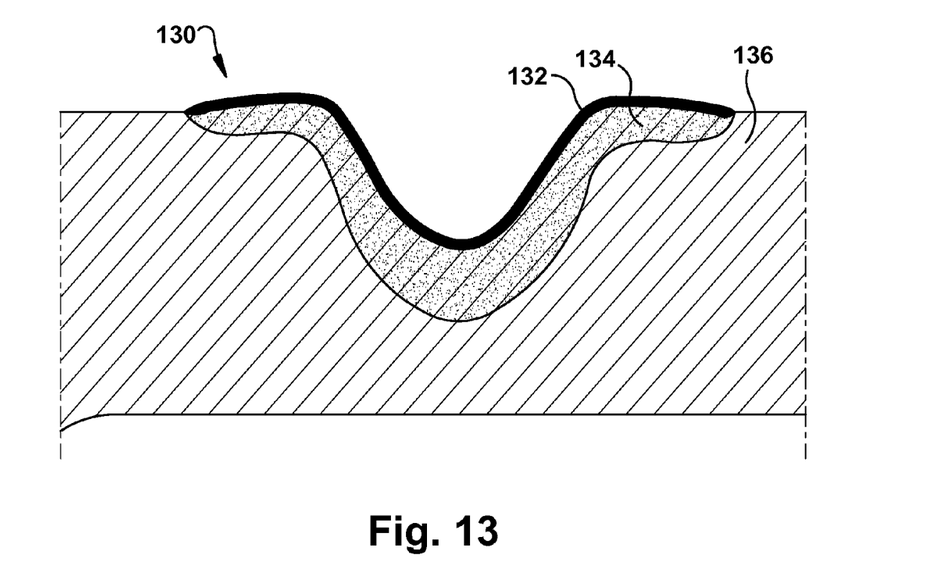
FIG. 13 is a cross-sectional schematic illustration of an SEM photograph taken of a substrate with a conductive trace, according to an embodiment of the present invention.

An electronic pattern or trace was made in a substrate material made of yttria-stabilized tetragonal zirconia polycrystal (Y-TZP) which comprises at least 99% by weight Zirconium oxide/Hafnium Oxide plus yttrium oxide ($ZrO_2 HfO_2+Y_2O_3$) available from C5 MedicalWerks, Kyocera, Morgan Technical Ceramics of Grand Junction, Colo. The biocompatible material was welded using a 30 Watt, CO2 laser which had an intensity of about 0.75 Joules. Three direct pulses were made on the surface of the substrate under ambient conditions (approximately 23 C). FIG. 13 is a cross-sectional schematic illustration of an SEM photograph that was taken of a medical device or component 130 with a conductive trace so formed. FIG. 13 shows the resulting trace 132 of elemental zirconium which was approximately 0.0005-0.002 inches deep and approximately 0.010-0.02 inches wide at the widest opening. Laser-affected-zone (LAZ) 134 resided between the conductive trace and the bulk material comprising zirconium oxide.

Figure 14:
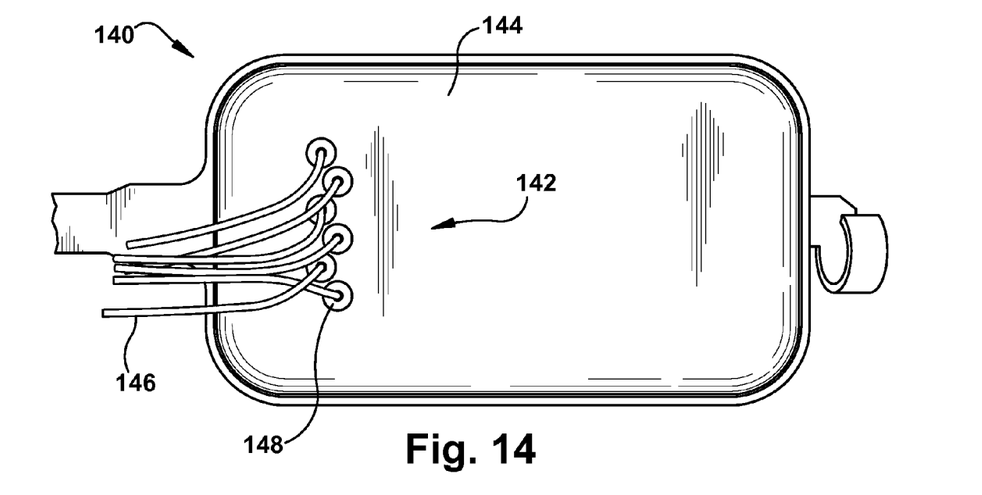
FIG. 14 is a top view schematic illustration of an SEM photograph taken of an electronics enclosure with a feedthrough assembly, according to an embodiment of the present invention.

FIG. 14 is a FIG. 14 is a top view schematic illustration of an SEM photograph taken of an electronics enclosure 140 with a feedthrough assembly 142, according to an embodiment of the present invention. A conductive path is formed between wires 146 connected to substrate 144 at wire heads 148 and through intrinsic conductive pathway of the enclosure to the electronics inside the enclosure.

From the above description of the invention, those skilled in the art will perceive improvements, changes and modifications. Such improvements, changes and modifications within the skill of the art are intended to be covered by the appended claims.

Having described the invention, the following is claimed:

1. A method for laser processing comprising:
applying a laser beam to a biocompatible material of an implantable medical device in an oxygen-free environment, wherein the material comprises at least about 50% by weight zirconium oxide under conditions sufficient to deplete the material of oxygen and convert the zirconium oxide to elemental zirconium at an interface where the laser beam is applied to the biocompatible material.

2. The method of claim 1, wherein the biocompatible material comprises, by weight, from about 0.1% to about 5% yttrium.

3. The method of claim 1, wherein the biocompatible material comprises less than about 5% impurities.

4. The method of claim 1, wherein the biocompatible material comprises, by weight, from about 85% to about 99% zirconium oxide.

5. The method of claim 1, wherein the implantable medical device is a component of a neurostimulator unit.

6. The method of claim 1, further comprising pre-heating the biocompatible material to a temperature in which the laser temperature does not thermally shock the biocompatible material prior to applying the laser beam to the biocompatible material.

7. The method of claim 1, further comprising cooling the biocompatible material of the implantable medical device after applying the laser beam, at a rate that prevents cracking of the zirconium oxide in the laser affected zone.

8. The method of claim 1, wherein the oxygen-free environment comprises a gas selected from the group consisting of: argon, helium, carbon dioxide, hydrogen, nitrogen and mixtures thereof.

9. The method of claim 1, wherein the oxygen-free environment comprises an amount of gas sufficient to eliminate the ingress of oxygen to the biocompatible material of the implantable medical device.

10. The method of claim 1, wherein the oxygen-free environment is a vacuum.

11. An implantable medical device made in accordance with the method of claim 1.

12. A method for laser processing an implantable medical device comprising:
applying a laser beam near opposing surfaces of an implantable medical device in an oxygen-free environment, wherein the opposing surfaces each comprise, by weight, at least about 50% by weight zirconium oxide sufficient to deplete the material of oxygen and convert the zirconium oxide to elemental zirconium at an interface where the laser beam is applied to the biocompatible material; and
joining the opposing material interfaces.

13. The method of claim 12, wherein the implantable medical device is hermetically sealed having an outflow of less than about $1 \times 10^{-9}$ atm.cc/s helium in accordance with at least one of standards Mil-std-883, BS9000, IEC749 and Mil 202F.

14. A method for laser processing comprising:
applying a laser beam to a material surface of an implantable medical device in an oxygen-free environment, wherein the device is made of a biocompatible material comprising, by weight, at least about 50% by weight zirconium oxide; and
forming a pattern of elemental zirconium on the material surface.

15. The method of claim 14, wherein forming the pattern comprises moving the surface of the implantable medical device relative to the laser beam or moving the laser beam relative to the surface of the implantable medical device.

16. The method of claim 14, wherein the pattern of elemental metal is electrically conductive.

17. A method for laser processing comprising:
applying a laser beam onto a first surface of a material comprising, by weight, at least 50% by weight zirconium oxide in an oxygen-free environment to form a first channel surface of zirconium; and
applying a laser beam onto a second surface of the material in an oxygen-free environment to form a second channel surface of zirconium that contacts the first channel surface of zirconium to produce an intrinsic conductive pathway of the device.

* * * * *